US012661334B2

(12) United States Patent
Patin et al.

(10) Patent No.: US 12,661,334 B2
(45) **Date of Patent: *Jun. 23, 2026**

(54) DIETARY BUTYRATE AND ITS USES

(71) Applicant: SOCIETE DES PRODUITS NESTLE S.A., Vevey (CH)

(72) Inventors: Amaury Patin, Lausanne (CH); Elizabeth Forbes-Blom, Epalinges (CH); Sameer Kulkarni, Copenhagen (DK)

(73) Assignee: Societe des Produits Nestle S.A., Vevey (CH)

( * ) Notice: Subject to any disclaimer, the term of this patent is extended or adjusted under 35 U.S.C. 154(b) by 1227 days.

This patent is subject to a terminal disclaimer.

(21) Appl. No.: 17/595,516

(22) PCT Filed: May 20, 2020

(86) PCT No.: PCT/EP2020/064074
§ 371 (c)(1),
(2) Date: Nov. 18, 2021

(87) PCT Pub. No.: WO2020/234351
PCT Pub. Date: Nov. 26, 2020

(65) Prior Publication Data

US 2022/0218646 A1 Jul. 14, 2022

(30) Foreign Application Priority Data

May 21, 2019 (EP) .................................... 19175536

(51) Int. Cl.
*A61K 31/231* (2006.01)
*A61P 3/06* (2006.01)

(52) U.S. Cl.
CPC .............. *A61K 31/231* (2013.01); *A61P 3/06* (2018.01)

(58) Field of Classification Search
None
See application file for complete search history.

(56) References Cited

U.S. PATENT DOCUMENTS 5,662,953 A 9/1997 Wheeler et al.

FOREIGN PATENT DOCUMENTS

| | | | |
|---|---|---|---|
| WO | WO-9109597 A1 * | 7/1991 | ............. A61P 43/00 |
| WO | WO 1991009597 A1 * | 7/1991 | |
| WO | 2006085346 | 8/2006 | |

OTHER PUBLICATIONS

Mandoe, M. et al. Comparing olive oil and C4-dietary oil, a prodrug for the GPR119 agonist, 2-oleoyl glycerol, less energy intake of the latter is needed to stimulate incretin hormone. Nutr & Diabetes 8, 2 (2018) (Year: 2018).*

Raso et al. Effects of sodium butyrate and its synthetic amide derivative on liver inflammation and glucose tolerance in an animal model of steatosis induced by high fat diet. PLoS One, 2013, 8, 5, e68626 (Year: 2013).*

Lam, B. et al. Treatment options for nonalcoholic fatty liver disease. Ther Adv Gastroenterol 2010 3(2):121-137 (Year: 2010).*

Seghieri, M. et al. Front. Future Perspectives on GLP-1 Receptor Agonists and GLP-1/glucagon Receptor Co-agonists in the Treatment of NAFLD Endocrinol, 2018, 9, 649 (Year: 2018).*

Arvanitakis, K. et al. GLP-1 Receptor Agonists in Obese Patients with Inflammatory Bowel Disease: from Molecular Mechanisms to Clinical Considerations and Practical Recommendations for Safe and Effective Use Curr Obes Rep 12, 61-74, 2023. (Year: 2023).*

Emerenziani, S. et al. Role of Overweight and Obesity in Gastrointestinal Disease. Nutrients 2020, 12, 111 (Year: 2020).*

(Continued)

*Primary Examiner* — Clinton A Brooks
*Assistant Examiner* — Nicola Maria Bauer
(74) *Attorney, Agent, or Firm* — K&L Gates LLP

(57) ABSTRACT

Use of a compound having the formula (1), (2), (3) or (4), or combinations thereof, for providing a source of butyrate with improved organoleptic properties wherein $R^1$, $R^2$, $R^3$, $R^4$, $R^5$ and $R^6$ are independently a long chain fatty acid having between 16 and 20 carbons the prevention and/or treatment of non alcoholic fatty liver disease.

(1)

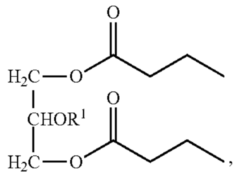

, (2)

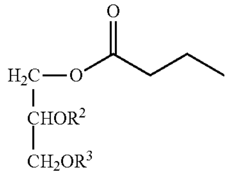

, (3)

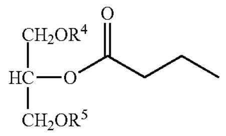

or (4)

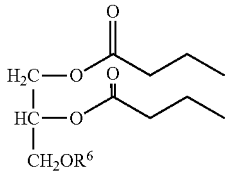

8 Claims, 2 Drawing Sheets

(56) References Cited

OTHER PUBLICATIONS

Neves, J. et al. Increased Risk of Heart Failure Hospitalization With GLP-1 Receptor Agonists in Patients With Reduced Ejection Fraction: A Meta-Analysis of the EXSCEL and FIGHT Trials Journal of Cardiac Failure, 29, 7, 2023 (Year: 2023).*
Soeters, M. et al. Effects of Insulin on Ketogenesis FollowingFasting in Lean and Obese Men. Obesity, 2009, 17(7):1326-31 (Year: 2009).*
Tallis, J. et al. The effects of obesity on skeletal muscle contractile function. J Exp Biol, 2018, 221(Pt 13):jeb163840 (Year: 2018).*
Jiang, W. Dysbiosis gut microbiota associated with inflammation and impaired mucosal immune function in intestine of humans with non-alcoholic fatty liver disease. Sci Rep, 2015, 5, 8096 (Year: 2015).*
Jiang, W. Sci Rep, 2015, 5, 8096 (Year: 2015).*
Mandoe, M. et al. Nutr & Diabetes 8, 2 (2018) (Year: 2018).*
Raso et al. PLoS One, 2013, 8, 5, e68626 (Year: 2013).*
Lam, B. et al. Ther Adv Gastroenterol 2010 3(2):121-137 (Year: 2010).*
Seghieri, M. et al. Front. Endocrinol, 2018, 9, 649 (Year: 2018).*
Jin et al. "Supplementation of sodium butyrate protects mice from the development of non-alcoholic steatohepatitis (NASH)" British Journal of Nutrition, 2015, vol. 114, No. 11, pp. 1745-1755.
Planchon et al. "Differential Elimination of Synthetic Butyric Triglycerides In Vivo: A Pharmacokinetic Study" Journal of Pharmaceutical Sciences, 1993, vol. 82, No. 10, pp. 1046-1048.
Raso et al. "Effects of Sodium Butyrate and Its Synthetic Amide Derivative on Liver Inflammation and Glucose Tolerance in an Animal Model of Steatosis Induced by High Fat Diet" PLoS One, 2013, vol. 8, No. 7, 10 pages.
Endo et al. "Butyrate-Producing Probiotics Reduce Nonalcoholic Fatty Liver Disease Progression in Rats: New Insight into the Probiotics for the Gut-Liver Axis" PLoS One, 2013, vol. 8, No. 5, 14 pages.
Acquistapace et al. "Effects of interesterified lipid design on the short/medium chain fatty acid hydrolysis rate and extent (in vitro)" Food & Function, 2019, vol. 10, No. 7, pp. 4166-4176.
Hayes et al. "Review of Triacylglycerol Digestion, Absorption, and Metabolism with Respect to SALATRIM Triacylglycerols" Journal of Agricultural and Food Chemistry, 1994, vol. 42, No. 2, pp. 474-483.
Sampugna et al. "Digestion of Butyrate Glycerides by Pancreatic Lipase" Lipids, 1967, vol. 2, No. 5, pp. 397-402.
Clement et al. "Action of Human Pancreatic Lipase on Synthetic Mixed Symmetrical Triglycerides of Long-Chain Acids and Butyric Acid" Biochemical and Biophysical Research Communications, 1962, vol. 8, No. 3, pp. 238-242.
Whitten et al., "Application of Chemoenzymatic Hydrolysis in the Synthesis of 2-Monoacylglycerols", Tetrahedron, vol. 68, 2012, pp. 5422-5428.
Japanese Office Action for Appl No. 2021-566103 dated May 14, 2024, 4 pages.

* cited by examiner

DIETARY BUTYRATE AND ITS USES

CROSS REFERENCE TO RELATED APPLICATIONS

The present application is a National Stage of International Application No. PCT/EP2020/064074, filed on May 20, 2020, which claims priority to European Patent Application No. 19175536.2, filed on May 21, 2019, the entire contents of which are being incorporated herein by reference.

FIELD OF THE INVENTION

The present invention relates novel uses of a dietary source of butyrate having improved organoleptic properties. In particular, the present invention provides a dietary source of butyrate having improved organoleptic properties and its uses in the prevention and/or treatment of non alcoholic fatty liver disease.

BACKGROUND TO THE INVENTION

Salts and esters of butyric acid are known as butyrates or butanoates. Butyric acid in ester form is found in many foods such as milk, especially goat, sheep, cow, camel and buffalo milk, and milk-derived products such as butter as well as cheeses such as parmesan cheese. Butyric acid is also a product of anaerobic fermentation, for example, as a product of fermentation produced by gut microbiota. Tributyrin is a triglyceride made of three ester functional groups with three butyrate moieties and the glycerol backbone. Under hydrolysis conditions such as those occurring during digestion, tributyrin is potentially a source of three moles of butyric acid per mole of tributyrin. However, the efficacy of tributyrin is potentially limited by its rapid gastric lipolysis.

The multiple beneficial effects of butyrate are well documented in mammals and livestock. At the intestinal level, butyrate plays a regulatory role on transepithelial fluid transport, mucosal inflammation and oxidative status, reinforces intestinal barrier function, and influences visceral sensitivity and intestinal motility.

Butyrate has been shown to improve the intestinal structure of piglets with short-bowel syndrome (Bartholome et al., J of Parenter Enteral Nutr. 2004; 28(4):210-222) and decrease the proliferation of colon cancer cells in human cell lines (Lupton, J Nutr., 2004; 134(2):479-482). The production of volatile fatty acids such as butyric acid from fermentable fibers may contribute to the role of dietary fiber in colon cancer (Lupton, The Journal of Nutrition. 134 (2): 479-82). Short-chain fatty acids (SCFA), which include but are not restricted to acetic, propionic and butyric acid, are produced by colonic bacteria that feed on, or ferment non-digestible fiber and/or prebiotics. SCFA, and most notably butyrate, promote regulatory T cells in the colon via histone deacetylase inhibition at the Foxp3 locus (Furusawa Y, et al., Nature 2013; 504(7480):446-450). Oral butyrate supplementation promotes antibacterial activity in intestinal macrophages and restricts dissemination of bacteria beyond the intestinal barrier. Butyric acid also benefits the colonocytes by increasing energy production. Additionally, butyrate has been shown to decrease the incidence of diarrhea (Berni Canani et al., Gastroenterol., 2004; 127(2): 630-634), improve gastrointestinal symptoms in individuals with diarrhea-predominant irritable bowel syndrome (Scarpellini et al., Dig Liver Dis., 2007; 1(1):19-22) and enhance the development of the small intestine in neonatal piglets (Kotunia et al., J Physiol Pharmacol. 2004; 55(2): 59-68).

Dietary supplementation of butyrate can prevent and treat diet-induced insulin resistance in mouse (Gao et al 2009).

Butyrate, produced by fermentation in the large intestine by gut microbiota has been demonstrated to be protective against insulin resistance and fatty liver (Mollica et al, 2017).

Published results also demonstrate a protective effect in limiting molecular events underlying the onset of non alcoholic fatty liver disease, suggesting a potential clinical relevance for this substance (Raso, G M et al, 2013).

Butyric acid and tributyrin are both food additives that are generally regarded as safe (GRAS) (21CFR582.60 and 21CFR184.1903 respectively), and are natural components of many dairy items. However, butyric acid is associated with negative sensory qualities such as vomit-like, fecal, and cheesy aroma attributes. Tributyrin also has negative sensory qualities, in particular high bitterness. These unpleasant taste and odor attributes can make the oral administration of compositions including these compounds particularly difficult, especially in the pediatric population.

Accordingly, it would be beneficial to provide a food-grade source of butyrate having improved organoleptic properties as compared to available solutions for use in the prevention and/or treatment of non alcoholic fatty liver disease.

SUMMARY OF THE INVENTION

The present invention provides compounds that are a source of butyrate having improved organoleptic properties for use in the prevention and/or treatment of non alcoholic fatty liver disease.

In particular, the compounds have improved odor and/or taste relative to butyric acid, butyrate salts and tributyrin. The compounds may be used as a dietary source of butyric acid. The compounds may be used in, for example, nutritional compositions, dietary supplements, infant formulas and follow-on formulas.

Advantageously compounds for use according to the present invention have been found to exhibit low extent of gastric lipolysis and may provide an effective delivery of butyric acid to the intestinal compartment.

According to one aspect of the present invention there is provided a compound having the formula (1)

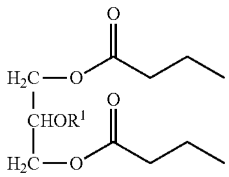

, (2)

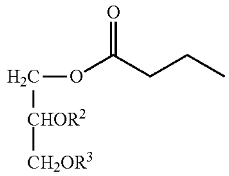

,

-continued (3)

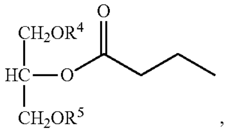

, or (4)

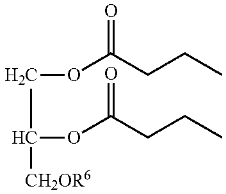

, or combinations thereof, for use in the prevention and/or treatment of non alcoholic fatty liver disease, wherein $R^1$, $R^2$, $R^3$, $R^4$, $R^5$ and $R^6$ are independently a long chain fatty acid having between 16 and 20 carbons.

According to another aspect of the present invention there is provided a method preventing and/or treating non alcoholic fatty liver disease in a patient comprising administering an effective amount of a compound having the formula (1)

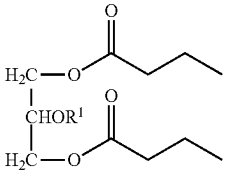

, (2)

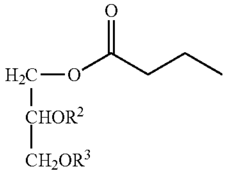

, (3)

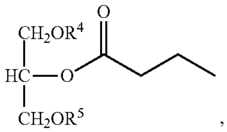

, or (4)

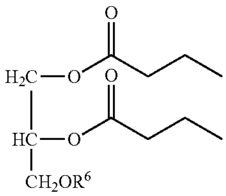

, or combinations thereof to said patient, wherein $R^1$, $R^2$, $R^3$, $R^4$, $R^5$ and $R^6$ are independently a long chain fatty acid having between 16 and 20 carbons.

In one embodiment, a combination of a compound having formula (1) and a compound having formula (2) is used as defined herein, or is present in the composition (e.g., nutritional composition, dietary supplement, infant formula or follow on formula) as defined herein. Preferably the compound having formula (1) is present in an amount of at least 10% by weight of the total triglycerides in the composition, and the compound having formula (2) is present in an amount of at least 10% by weight of the total triglycerides in the composition.

In one embodiment a combination of a compound having formula (1) and a compound having formula (2) is used as defined herein, or is present in the composition (e.g., nutritional composition, dietary supplement, infant formula or follow-on formula) as defined herein, wherein the compound having formula (1) is present in an amount of at least 10% by weight of the total butyric acid containing triglycerides in the composition, and the compound having formula (2) is present in an amount of at least 10% by weight of the total butyric acid containing triglycerides in the composition.

In another embodiment a combination of a compound having formula (1) and a compound having formula (2) is used as defined herein, or is present in the composition (e.g., nutritional composition, dietary supplement, infant formula or follow on formula) as defined herein wherein the compound having formula (1) is present in an amount of at least 15% by weight of the total butyric acid containing triglycerides in the composition, and the compound having formula (2) is present in an amount of at least 15% by weight of the total butyric acid containing triglycerides in the composition.

In one embodiment a combination of a compound having formula (1), a compound having formula (2), a compound having formula (3) and a compound having formula (4) is used as defined herein, or is present in the composition, nutritional composition, dietary supplement, infant formula or follow on formula as defined herein.

In one embodiment, $R^1$, $R^2$, $R^3$, $R^4$, $R^5$ and/or $R^6$ as defined herein is an unsaturated fatty acid, preferably monounsaturated.

In one embodiment, $R^1$, $R^2$, $R^3$, $R^4$, $R^5$ and/or $R^6$ as defined herein is selected from the group consisting of oleic acid, palmitic acid, stearic acid or linoleic acid.

In one embodiment, $R^1$, $R^2$, $R^3$, $R^4$, $R^5$ and/or $R^6$ as defined herein is oleic acid.

In one embodiment, $R^1$, $R^2$, $R^3$, $R^4$, $R^5$ and/or $R^6$ as defined herein is palmitic acid.

In one embodiment the compound (1) is 1,3-dibutyryl-2-palmitoylglycerol.

In one embodiment, each of $R^1$, $R^2$, $R^3$, $R^4$, $R^5$ and $R^6$ is oleic acid.

In one embodiment, the compound having the formula (1) is:

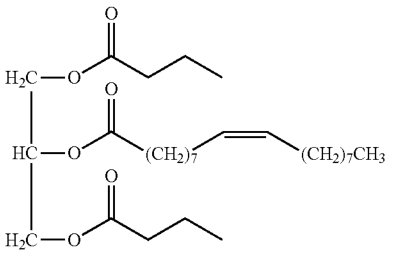

In one embodiment, the compound having the formula (2) is:

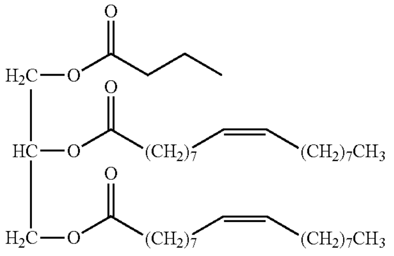

In one embodiment, the compound having the formula (3) is:

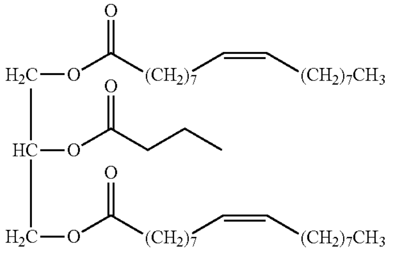

In one embodiment, the compound having the formula (4) is:

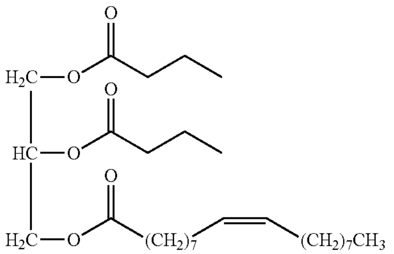

According to another aspect of the present invention there is provided a composition for use in the prevention and/or treatment of non alcoholic fatty liver disease comprising compounds having the formulas (5)

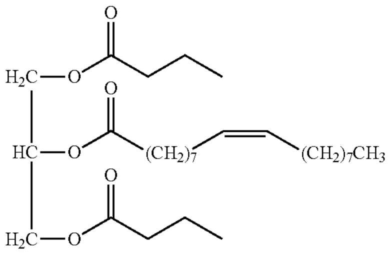

and

-continued (6)

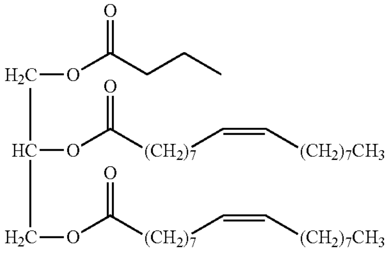

wherein the compound having formula (5) comprises at least 10% by weight of the total triglycerides in the composition, and the compound having formula (6) comprises at least 10% by weight of the total triglycerides in the composition.

In one embodiment the compound having formula (5) comprises at least 15% by weight of the total triglycerides in the composition, and the compound having formula (6) comprises at least 15% by weight of the total triglycerides in the composition.

In one embodiment the compound having formula (5) comprises at least 15% by weight of the total triglycerides in the composition, and the compound having formula (6) comprises at least 20% by weight of the total triglycerides in the composition.

In one embodiment the compound having formula (5) comprises at least 20% by weight of the total triglycerides in the composition, and the compound having formula (6) comprises at least 20% by weight of the total triglycerides in the composition.

In one embodiment the compound having formula (5) comprises about 15% to about 30% by weight of the total triglycerides in the composition, and the compound having formula (6) comprises about 20% to about 30% by weight of the total triglycerides in the composition.

In one embodiment the composition for use in the prevention and/or treatment of non alcoholic fatty liver disease further comprises a compound having the formula (7)

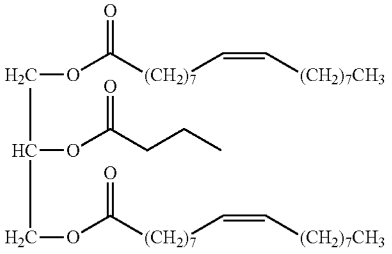

preferably wherein the compound having formula (7) comprises at least 2% or 3% by weight of the total triglycerides in the composition, and/or further comprises a compound having the formula (8)

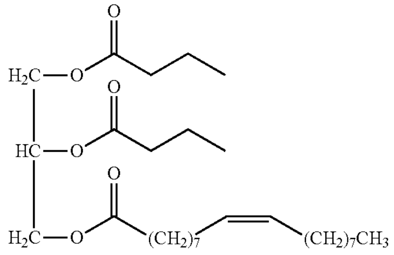

preferably wherein the compound having formula (8) comprises at least 2% or 3% by weight of the total triglycerides in the composition.

According to another embodiment of the present invention there is provided a composition for use in the prevention and/or treatment of non alcoholic fatty liver disease comprising compounds having the formulas (5)

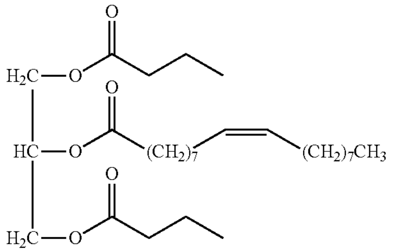

and (6)

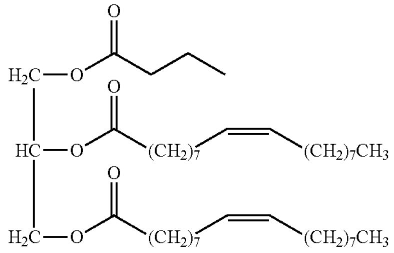

wherein the compound having formula (5) comprises at least 10% by weight of the total butyrate moiety containing triglycerides in the composition, and the compound having formula (6) comprises at least 10% by weight of the total butyrate moiety containing triglycerides in the composition.

In one embodiment, the compound having formula (5) comprises at least 15% by weight of the total butyrate moiety containing triglycerides in the composition, and the compound having formula (6) comprises at least 15% by weight of the total butyrate moiety containing triglycerides in the composition.

In one embodiment, the compound having formula (5) comprises at least 15%, preferably at least 20% by weight of the total butyrate moiety containing triglycerides in the composition, and the compound having formula (6) comprises at least 20%, preferably at least 25% by weight of the total butyrate moiety containing triglycerides in the composition.

In one embodiment the composition for use in the prevention and/or treatment of non alcoholic fatty liver disease further comprises a compound having formula (7), preferably wherein the compound having formula (7) comprises at least 2% or 3% by weight of the total butyrate moiety containing triglycerides in the composition, and/or further comprises the compound having formula (8), preferably wherein the compound having formula (8) comprises at least 2% or 3% by weight of the total butyrate moiety containing triglycerides in the composition.

The composition of the present invention for use in the prevention and/or treatment of non alcoholic fatty liver disease may further comprise 1,3-dibutyryl-2-linoleoylglycerol, 1,3-dibutyryl-2-stearoylglycerol, 1-butyryl-2-oleoyl-3-palmitoylglycerol, 1-palmitoyl-2-oleoyl-3-butyrylglycerol, 1-butyryl-2-oleoyl-3-inoleoylglycerol, 1-linoleoyl-2-oleoyl-3-butyrylglycerol, 1-oleoyl-2-butyryl-3-linoleoylglycerol, 1-linoleoyl-2-butyryl-3-oleoylglycerol, 1-butyryl-2-linoleoyl-3-oleoylglycerol, 1-oleoyl-2-linoleoyl-3-butyrylglycerol, 1-butyryl-2-stearoyl-3-oleoylglycerol, 1-oleoyl-2-stearoyl-3-butyrylglycerol, 1-butyryl-2-oleoyl-3-stearoylglycerol, 1-stearoyl-2-oleoyl-3-butyrylglycerol, 1,2-dioleoyl-3-palmitoylglycerol, 1-palmitoyl-2,3-dioleoylglycerol, 1,2-dioleoyl-3-linoleoylglycerol and/or 1-linoleoyl-2,3-dioleoylglycerol.

The composition for use according to the present invention may be in the form of nutritional composition.

The composition for use according to the present invention may be in the form of an infant formula or follow on formula.

The composition for use according to the present invention may be in the form of dietary supplement.

According to another aspect of the present invention there is provided a method of providing a source of butyric acid with improved organoleptic properties to a subject, said method comprising administering an effective amount of a composition defined herein to said subject.

According to another aspect of the present invention there is provided a method of preventing and/or treating non alcoholic fatty liver disease in a subject comprising administering an effective amount of a composition defined herein to a subject.

SHORT DESCRIPTION OF THE FIGURES

DETAILED DESCRIPTION OF THE INVENTION

Triglycerides

Figure 1:
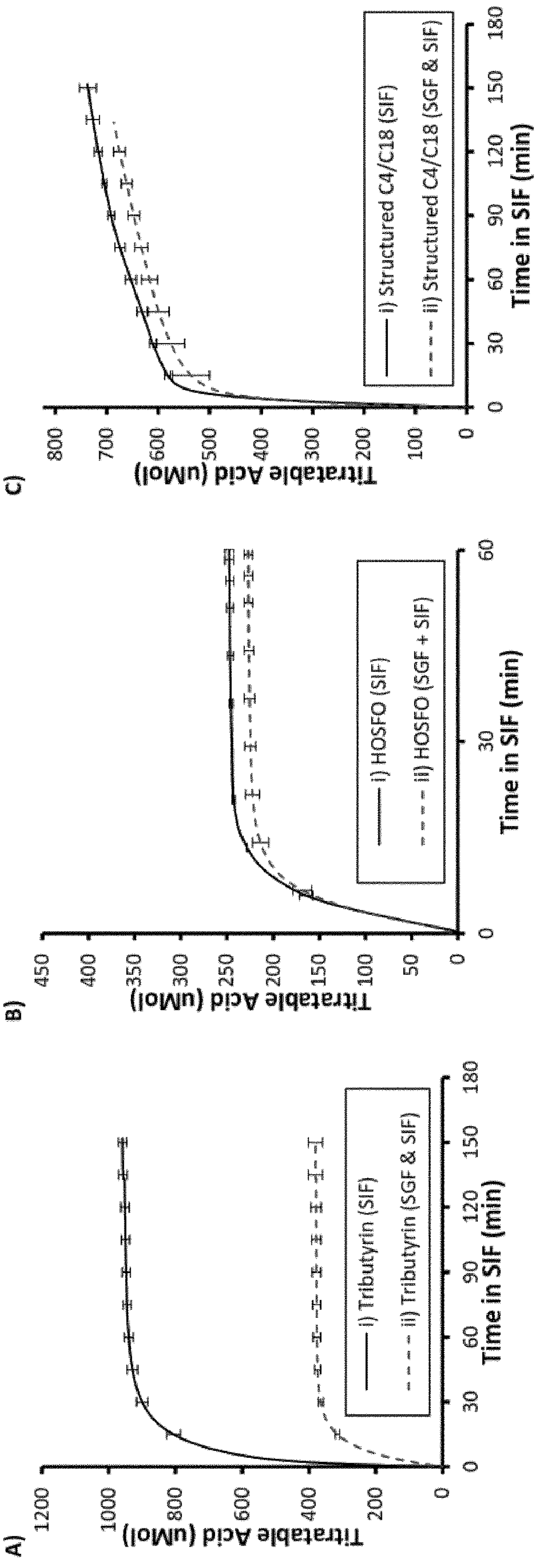
FIG. 1 shows the release of fatty acid from emulsions containing 200 mg of (A) tributyrin, (B) high oleic sunflower oil and (C) a mixture of butyrate moiety containing triacylglycerol (TAG) according to the invention, digested either with i) simulated intestinal fluid (SIF) or (ii) sequentially with gastric fluid (SGF) followed by simulated intestinal fluid (SIF).

A triglyceride (also known as a triacylglycerol) is a triester that is derived from glycerol and three fatty acids.

Fatty acids are carboxylic acids with a long tail (chain). Fatty acids may be either unsaturated or saturated. Fatty acids which are not attached to other molecules are referred to as free fatty acids (FFA).

The term "fatty acid moiety" refers to the part of the triglyceride that originates from a fatty acid in an esterification reaction with glycerol. The triglycerides used in the present invention comprise at least one butyric acid moiety and at least one long chain fatty acid moiety.

Preferred long chain fatty acids for use in the present invention are fatty acids that have 16 to 20 carbon atoms.

Examples of long chain fatty acid include oleic acid, palmitic acid, stearic acid and linoleic acid.

The triglycerides of the present invention may be synthesised by, for example, esterification of long chain fatty acid(s) and butyric acid with glycerol.

The triglycerides of the present invention may be synthesised by, for example, interesterification between tributyrin and another triglyceride containing long chain fatty acids. In one embodiment, high oleic sunflower oil is the source of the long chain fatty acids. This generates triglycerides containing predominantly butyrate and oleate moieties. Oleic acid is the predominant fatty acid present in breast milk. The compounds are dairy-free, cholesterol-free and vegan. Fatty acids are liberated from triglycerides due to lipases, naturally present in the gastrointestinal tract. Relative to butyrate salts, the compounds do not add additional mineral salts to the final formulation.

Alternative methods of triglyceride synthesis can be routinely determined by a person skilled in the art. By way of example, a method of obtaining 1,3-dibutyryl-2-palmitoylglycerol (BPB) is shown below:

composition" that is to say a foodstuff that involves the gastrointestinal tract for its administration. The gastric introduction may involve the use of a tube through the oro/nasal passage or a tube in the belly leading directly to the stomach. This may be used especially in hospitals or clinics. The composition of the invention can be administered to an individual such as a human, e.g., an elderly human an infant, a child and/or an adult, in a therapeutically effective dose. The therapeutically effective dose can be determined by the person skilled in the art and will depend on a number of factors known to those of skill in the art, such as the severity of the condition and the weight and general state of the individual.

The term "dietary supplement" may be used to complement the nutrition of an individual (it is typically used as such but it might also be added to any kind of compositions intended to be ingested). It may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents,

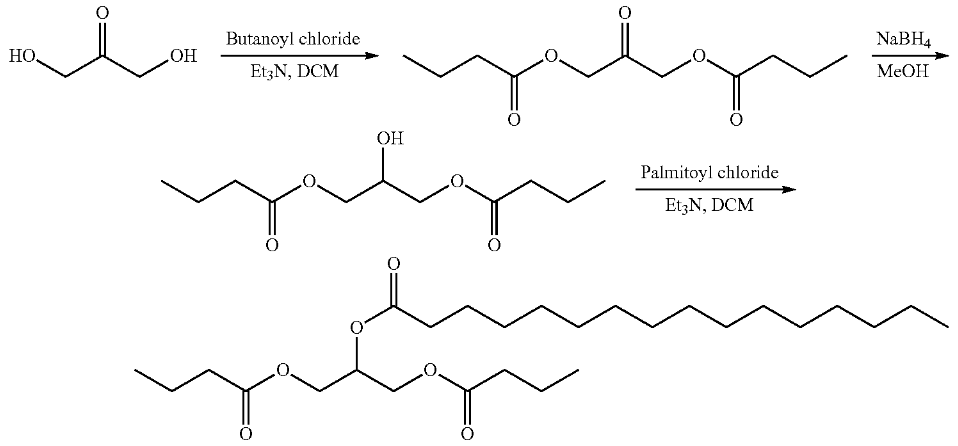

A single butyrate moiety containing triglyceride may be used herein. Alternatively, a mixture of different butyrate moiety containing triglycerides may be used.

Compositions

The present invention provides compositions comprising butyrate moiety containing triglycerides referred to herein. The composition may be, for example, a nutritional composition, a dietary supplement.

The expression "nutritional composition" means a composition that nourishes a subject. This nutritional composition is preferably taken orally, and it may include a lipid or fat source and a protein source. It may also contain a carbohydrate source. In one embodiment, the nutritional composition contains only a lipid or fat source. In other specific embodiments, the nutritional composition contains a lipid (or fat) source with a protein source, a carbohydrate source or both.

In some specific embodiments, the nutritional composition according to the invention is an "enteral nutritional taste masking agents, weighting agents, jellifying agents and gel forming agents. The dietary supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

When the composition is a supplement, it can be provided in the form of unit doses.

The nutritional composition of the invention generally contains a protein source, a carbohydrate source and a lipid source. In some embodiments however, especially if the nutritional composition of the invention is a supplement or a fortifier, there may be only lipids (or a lipid source).

The nutritional composition according to the invention may contain a protein source. The protein may be in an amount of from 1.6 to 3 g per 100 kcal. In some embodiments, especially when the composition is intended for preterm infants/young children, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal. Protein sources based on, for example, whey, casein and mixtures thereof may be used as well as plant based protein sources, for example, based on soy. As far as whey proteins are concerned, the protein source may be based on acid whey or sweet whey or mixtures thereof and may include alpha-lactalbumin and beta-lactoglobulin in any desired proportions. In some embodiments the protein source is whey predominant (i.e. more than 50% of proteins are coming from whey proteins, such as 60%> or 70%>). The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10%> by weight of lysine; for example about 7% by weight of lysine which greatly improves the nutritional quality of the protein source.

In one particular embodiment the proteins of the composition are hydrolysed, fully hydrolysed or partially hydrolysed. The degree of hydrolysis (DH) of the protein can be between 2 and 20, or between 8 and 40, or between 20 and 60 or between 20 and 80 or more than 10, 20, 40, 60, 80 or 90. For example, nutritional compositions containing hydrolysates having a degree of hydrolysis less than about 15% are commercially available from Nestle Company under the trade mark Peptamen®.

At least 70%, 80%, 85%, 90%, 95% or 97% of the proteins may be hydrolysed. In a particular embodiment, 100% of the proteins are hydrolysed.

In one particular embodiment the proteins of the composition are plant based protein.

The nutritional composition according to the present invention may contain a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates for infant formula is lactose. The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B3, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population. If necessary, the nutritional composition of the invention may contain emulsifiers and stabilisers such as soy, lecithin, citric acid esters of mono- and diglycerides, and the like. The nutritional composition of the invention may also contain other substances which may have a beneficial effect such as lactoferrin, osteopontin, TGFbeta, sIgA, glutamine, nucleotides, nucleosides, and the like.

The composition of the invention can further comprise at least one non-digestible oligosaccharide (e.g. prebiotics). They are usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such as fructooligosaccharides (FOS), inulin, xylooligosaccharides (XOS), polydextrose or any mixture thereof. In a particular embodiment, the prebiotics may be fructooligosaccharides and/or inulin. In a specific embodiment, the prebiotics is a combination of FOS with inulin such as in the product sold by BENEO-Orafti under the trademark Orafti® oligofructose (previously Raftilose®) or in the product sold by BENEO-Orafti under the trademark Orafti® inulin (previously Raftiline®). Another example is a combination of 70% short chain fructooligosaccharides and 30% inulin, which is registered by Nestle under the trademark "Prebio 1". The nutritional composition of the invention can also comprise at least one milk oligosaccharide that can be a BMO (bovine milk oligosaccharide) and/or a HMO (human milk oligosaccharide). The composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is Bifidobacteria and/or *Lactobacilli.*

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. It may also be probiotic parts such as cell wall components or products of the probiotic metabolism. There may be both viable probiotics and inactivated probiotics in some other embodiments. The nutritional composition of the invention can further comprise at least one phage (bacteriophage) or a mixture of phages, preferably directed against pathogenic Streptococci, *Haemophilus, Moraxella* and Staphylococci.

The nutritional composition according to the invention may be prepared in any suitable manner.

For example, a formula such as an infant formula may be prepared by blending together the protein source, the carbohydrate source and the fat source, in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water that has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

Any oligosaccharides may be added at this stage, especially if the final product is to have a liquid form. If the final product is to be a powder, they may likewise be added at this stage if desired.

The liquid mixture is then homogenised, for example in two stages.

In one embodiment the nutritional composition of the invention is given to the infant or young child as a supplementary composition to the mother's milk.

The composition of the present invention can be in, for example, a solid (e.g. powder), liquid or gelatinous form.

The composition of the present invention can be in, for example, tablet, dragee, capsule, gel cap, powder, granule, solution, emulsion, suspension, coated particle, spray-dried particle or pill.

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients", 2nd Edition, (1994), Edited by A Wade and P J Weller. Acceptable carriers or diluents for therapeutic use are well known in the pharmaceutical art, and are described, for example, in Remington's Pharmaceutical Sciences, Mack Publishing Co. (A. R. Gennaro edit. 1985).

The pharmaceutical compositions may comprise as, or in addition to, the carrier, excipient or diluent any suitable binder(s), lubricant(s), suspending agent(s), coating agent(s) and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

The nutritional composition according to the present invention can in one embodiment be a food product.

Treatment

It is to be appreciated that all references herein to treatment include curative, palliative and prophylactic treatment. Treatment may also include arresting progression in the severity of a disease. Both human and veterinary treatments are within the scope of the invention.

Non Alcoholic Fatty Liver Disease

The multiple beneficial effects of butyrate on bone health have been documented in the scientific literature as reported in the background of the present invention.

The compounds defined herein are a source of butyrate/butyric acid and may therefore be used in the prevention and/or treatment of non alcoholic fatty liver disease.

Within the context of the present invention, the term "non-alcoholic fatty liver disease" means one or more of the following: non-alcoholic fatty liver (NAFL) and non-alcoholic steatohepatitis (NASH), liver fibrosis, cirrhosis, liver cancer and/or liver failure.

The term "prevention and/or treatment of non-alcoholic fatty liver disease" means the prevention and the reduction of frequency and/or occurrence and/or severity and/or duration of metabolic disorders. Occurrence is related to the number of any non alcoholic fatty liver disease. Frequency is related to the number of the same bone disease. This prevention encompasses the reduction of frequency and/or of severity of said bone disease later in life.

Administration

Preferably, the compounds and compositions described herein are administered enterally.

Enteral administration may be for example oral or gastric.

In general terms, administration of the combination or composition described herein may, for example, be by an oral route or another route into the gastro-intestinal tract, for example the administration may be by tube feeding.

The subject may be a mammal such as a human, canine, feline, equine, caprine, bovine, ovine, porcine, cervine and primates. Preferably the subject is a human.

Though the invention may be useful in many various mammal age groups, in one embodiment the compounds and compositions for use according to the invention are targeted to adults and/or ageing population.

In one embodiment, the compounds and compositions for use according to the invention are targeted to adults and/or ageing population at risk of developing non alcoholic fatty liver, for example obese, having Type2 diabetes and/or metabolic syndrome.

Organoleptic Properties

The present invention provides compounds that are a source of butyrate having improved organoleptic properties. In particular, the compounds have improved odor and/or taste relative to butyric acid, butyrate salts and/or tributyrin. In one embodiment, the compounds have improved taste relative to tributyrin. In one embodiment, the compounds have improved smell relative to butyrate salts (e.g. sodium butyrate).

In one embodiment, the improved organoleptic properties are improved odour. In one embodiment, the improved organoleptic properties are improved taste. In one embodiment, the improved organoleptic properties are improved odour and improved taste. In one embodiment, the improved taste is reduced bitterness.

EXAMPLES

Example 1—Preparation of Butyrate Moiety Containing Triglycerides

Compositions comprising butyrate moiety containing triglycerides were generated by chemical interesterification between tributyrin and high oleic sunflower oil in the presence of catalyst such as sodium methanoate. A molar excess of tributyrin compared to high oleic sunflower oil was used.

The three reagents, tributyrin, high oleic sunflower oil and the catalyst were mixed together into a reactor under nitrogen atmosphere and then heated under stirring at 80° C. for 3 h. Once the reaction is completed, the product was washed with water and dried under vacuum (25 mBar at 60° C. for 2 h). The resulting oil product was then subjected to a decoloration step with the action of bleaching earth and was purified either by short-path distillation (130° C., 0.001-0.003 mbar) and/or by deodorisation (160° C., 2 mbar, 2 h) with injection of steam water.

The constituents, mostly triglycerides, of the resulting oil compositions are shown below in Table 1. These triglycerides are represented by the three fatty acids they contain. These fatty acids are represented by their lipid number: 4:0 for butyrate, 16:0 for palmitate, 18:0 for stearate 18:1 for oleate and 18:2 for linoleate. The fatty acid in the middle is located on the position sn-2 in the triglyceride. As an example, 16:0-4:0-18:1 stands for two different triglycerides having both a butyrate in position sn-2 and either a palmitate in position sn-1 and an oleate in position sn-3 or an oleate in position sn-1 and a palmitate in position sn-3.

Triglyceride profile and regioisomers were analyzed by liquid chromatography coupled to high resolution mass spectrometer. Lipid classes' proportion was evaluated by liquid chromatography coupled to evaporative light scattering detector (ELSD).

TABLE 1

| Triglyceride regioisomer profile [g/100 g]<br>Triglyceride regioisomer [g/100 g]<br>Composition | |
|---|---|
| 4:0-4:0-4:0 | <0.4-4.7 |
| 4:0-16:0-4:0 | 0.8-1.0 |
| 4:0-18:2-4:0 | 4.0-6.3 |
| 4:0-4:0-18:1 | 3.0-6.1 |
| 4:0-18:1-4:0 | 16.2-27.0 |
| 4:0-18:0-4:0 | 0.8-1.3 |
| 4:0-22:0-4:0 | ≤0.4 |
| 4:0-16:0-18:1 | 1.1-1.5 |
| 16:0-4:0-18:1 | 0.5-0.7 |
| 4:0-18:1-16:0 | 1.2-1.6 |
| 4:0-18:1-18:2 | 2.6-3.1 |
| 18:1-4:0-18:2 | 1.1-1.6 |
| 4:0-18:2-18:1 | 2.9-3.6 |
| 18:1-18:1-4:0 | 23.3-25.8 |
| 18:1-4:0-18:1 | 3.3-4.8 |
| 4:0-18:0-18:1 | 0.9-1.3 |
| 4:0-18:1-18:0 | 0.8-1.1 |
| 4:0-22:0-18:1 | <0.4-0.5 |
| 18:1-18:1-16:0 | 0.6-1.4 |
| 18:1-18:1-18:2 | 1.3-1.5 |
| 18:1-18:2-18:1 | 0.5-0.7 |
| 18:1-18:1-18:1 | 6.1-10.7 |
| 18:1-18:1-18:0 | 0.5-0.8 |
| Total | 93.1-94.1 |

In the Composition samples, the two most abundant triglycerides are 4:0-18:1-4:0 and 18:1-18:1-4:0, they represent together approximately 40 to 50 g/100 g.

Example 2—Odour Properties of Butyrate Moiety Containing Triglycerides

An odour comparison of a solution including butyrate moiety containing triglycerides (composed mainly with oleic and butyric fatty acids) was compared to a solution containing sodium butyrate.

Sample Preparation

Solutions including butyrate moiety containing triglycerides (see Example 1) or sodium butyrate were prepared and stored at 4° C. prior to delivery to the sensory panel. Each 250 mL solution contained 600 mg of butyric acid (equivalent to one capsule of commercially available sodium butyrate as a supplement; 2.4 mg/mL concentration) and 1% w/v BEBA Optipro 1 infant formula in acidified, deionized water.

The samples were prepared the day before the test, by putting 4 mL of each solution (triglycerides butyrate solution; sodium butyrate solution) in Agilent vials.

Methodology

The 'two-out-of-five test' was performed. In this test, the panellist is given five samples. The panellist is instructed to identify the two samples that are different from the other three. The presentation order of the samples is randomized in order to avoid presentation order bias.

In addition to the two-out-of-five test, a comment box was presented to the panellists to allow them to comment about the nature of the difference perceived (e.g. odour intensity, odour quality).

Results

The five samples were presented simultaneously to the panellists. They were asked to uncap, smell and then cap each vial in a given order. The results are shown in Table 2.

TABLE 2

| Number of responses | Number of correct responses | Significance |
|---|---|---|
| 11 | 9 | $p < 0.0001$*** |

P-value was calculated using a binomial test performed with Fizz software (Biosystemes, France).

The panellists who found the correct responses (butyrate moiety containing TAG different from sodium butyrate) mentioned that the sodium butyrate smells "cheese" whereas for the butyrate moiety containing TAG samples this "cheese" smell was considerably decreased and the odour was quite neutral.

Example 3—Taste Properties of Butyrate Moiety Containing Triglycerides

Sensory benchmarking of a solution including butyrate moiety containing triglycerides (see Example 1) composed mainly with oleic and butyric fatty acids was performed versus a solution containing tributyrin.

Sample Preparation

One scoop (4.6 g) of BEBA Optipro 1 infant formula was added to warm water (cooled, boiled tap water as per instructions) to a final volume of 150 mL (approximately 3% w/v solution). Each triglyceride form of butyrate was weighed separately to deliver 600 mg of butyrate, and the addition of infant formula to a final volume of 50 mL for each solution was performed.

Solution A included butyrate moiety containing triglycerides (see Example 1); and solution B contained tributyrin.

Methodology

A group of panellists performed a repeated blind-coded tasting.

The samples were prepared just prior to the preliminary bitterness assessment, and each solution was vigorously shaken. Tasting cups labelled A and B were filled at the same time with a small volume of the respective solution.

The two samples were presented simultaneously to the panellists. They were asked to taste the solution in a sip and spit fashion, and rank the perceived bitterness on a scale from 0-10; where 0 is no bitterness perceived and 10 resembles the maximum imaginable bitterness.

Results

Bitterness of Solution A was ranked by panellists at 4.33±1.52, mean±SD.

Bitterness of Solution B was ranked by panellists at 8.33±1.52, mean±SD.

These data show that the butyrate moiety containing TAG composition in infant formula was notably less bitter in taste as compared to tributyrin.

Example 4—Taste Properties 1,3-dibutyryl-2-palmitoylglycerol 1,3-dibutyryl-2-palmitoylglycerol (BPB) was synthesized as a single compound using the following synthesis:

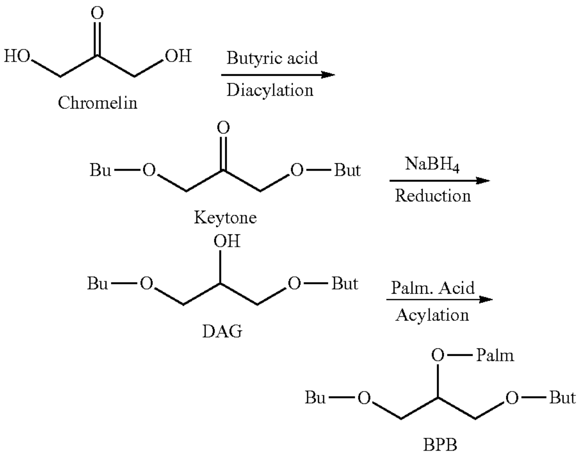

Chromelin
Keytone
DAG
BPB

BPB was evaluated in a descriptive sensory panel evaluation and found to be neutral in taste and odour.

Example 5—Digestion of Butyrate Moiety Containing Triglycerides

5.1 Materials

Sodium taurocholate, sodium chloride, hydrochloric acid, sodium hydroxide, potassium hydroxide, maleic acid, tris (hydroxymethyl)aminomethane,pepsin (Porcine, 800—111 2500 U/mg, P7000, actual activities used 674 U/mg and 561 U/mg), pancreatin (Porcine, USP×8, P7585) and bile extract porcine (total bile salt content=49 wt %; with 10-15% glycodeoxycholic acid, 3-9% taurodeoxycholic acid, 0.5-7% deoxycholic acid; phospholipids 5%, B8631) were used as obtained and were purchased from Sigma-Aldrich (St Louis, MO, USA). Rabbit gastric extract (RGE 70≥70 U/mL RGL and ≥280 U/mL pepsin) was purchased from Lipolytech (Marseille, France). All the water used in this study was of purified Milli Q quality. Tributyrin (Food grade) from Sigma, high oleic sunflower oil from Florin. Interesterified triglycerides were obtained via chemical interesterification with sodium methanoate (from Evonik) as catalyst.

5.2 Emulsion Preparation 10 wt % oil in water emulsions stabilised by 0.3 wt % polyoxyethylene sorbitan mono-oleate (Tween® 80) were prepared by mixing the Tween 80 into the oil phase at 40° C., then mixing with the water phase using a magnetic stirrer. An emulsion was then created using a Hielscher UP 400S ultrasonic probe homogeniser equipped with a 5 mm diameter rod-like probe by applying 100% amplitude at 100% cycle for 2 minutes whilst the sample was cooled using ice water.

5.3 Granulometry

The droplet size of each lipid emulsion was measured by laser light scattering using a Mastersizer 3000 equipped with a Hydro SM from Malvern Instruments (Malvern, Worcestershire, United Kingdom). The laser specifications of the two lasers are 4 mW 632.8 nm and 10 mW 470 nm. Samples were diluted to approximately 0.002 wt % in an effort to avoid multiple scattering effects. Information about emulsion particle size was then obtained via a best fit between light scattering (Mie) theory and the measured particle size distribution. A refractive index of 1.456 and an adsorption of 0.01 were used for the oil phase. Emulsion particle sizes are quoted as two values, the volume surface mean diameter D3,2 (D3,2 ¼ Pnidi 3/nidi 2) or the volume length mean diameter D4,3 (D4,3 ¼ Pnidi 4/nidi 3). Emulsion particle size results are an average of three measurements of two freshly prepared emulsions.

5.4 Statistical Analysis

Statistical analysis was conducted using a two sided t test with unequal variances using the software Igor Pro.

5.5 In Vitro Digestion

The lipid emulsion (2 mL) containing 200 mg of fat was subjected to gastrointestinal in vitro lipolysis. The digestions were conducted in thermostated glass vessels (37° C.) in a pH-STAT setup controlled by a TIM 856 bi-burette pH-STAT (Radiometer Analytical, France). For gastric digestion, the sample was incubated for 90 minutes with 8.5 mL of simulated gastric fluid (SGF), which consisted of 150 mM NaCl, 450 U/mL pepsin, 18 U/mL rabbit gastric lipase at 37° C. and a pH of 5.5. The digestion was initiated by adding 18 tributyrin U/ml (TBU) activity determined at pH 5.4) of rabbit gastric lipase.

The intestinal digestion step was performed in the pH stat where the pH was kept constant at 6.8 by addition of NaOH (0.05 M). A bile salt mixture (bile salts prepared with tris buffer, 5 mM tris, 150 mM NaCl) and calcium solution (20 mM Ca, 176 5 mM tris, 150 mM NaCl) were added to the SGF-sample mixture. This mixture was transferred to the pH-stat, where the pH was adjusted to approximately 6.78. The intestinal digestion step starts when the temperature reaches 37±0.5° C. The pH was adjusted to pH 6.8 and after incubation of two minutes at this pH and temperature, a pancreatin solution (5 mM tris, 150 mM NaCl at pH 6.8) was added. The final composition of the intestinal fluid was 10 mM $CaCl_2$, 12 mM mixed bile salts, 0.75 mM phospholipid, 150 mM NaCl and 4 mM tris(hydroxymethyl)aminomethane buffer. The intestinal digestion step was carried out for 3 hours in a titration manager from Radiometer. During the intestinal phase of digestion, the kinetics of digestion were followed using a pH-stat (TIM856, Radiometer) technique and expressed as titratable acid (rather than fatty acid) that was calculated by the equation:

$$TA=V_{NaOH}\times 0{:}05\times 1000$$

TA: Total titratable acid released, mmol; $V_{NaOH}$: volume of NaOH used to titrate the released acid in 3 h, mL.

5.6 Results

Since the digestion of dietary lipids involves lipases of both gastric and intestinal origin, lipid digestibility was assessed using two digestion models i) simulated intestinal fluid (SIF) with porcine pancreatic lipase (PPL) and ii) sequential digestion in simulated gastric fluid (SGF) with rabbit gastric lipase (RGL) followed by simulated intestinal fluid (SIF) with porcine pancreatic lipase (PPL). All lipids were emulsified using polyoxyethylene sorbitan monooleate (Tween® 80) and had similar particle size distributions and specific surface areas (FIG. 2), meaning the differences in digestion are predominately arising from the triglyceride molecular structure.

FIG. 1*i* A-C shows the digestion of tributyrin (C4), high oleic sunflower oil (HOSFO, largely C18:1) and butyrate moiety containing triglycerides according to the invention, generated by chemical interesterification between tributyrin and high oleic sunflower oil (see Example 1) "C4-C18:1", by porcine pancreatic lipase (from pancreatin) in the presence of mixed bile and calcium (SIF model). The lipids generally exhibit the same lipolysis behaviour, undergoing an initial rapid period of lipolysis during the first 15 minutes which progressively slows during the final 2.5 hours of simulated intestinal digestion. C4 triglyceride exhibited an initial maximal rates of lipolysis of 223±59 μmol·min$^{-1}$. The initial rate of lipolysis for the high oleic sunflower oil, 34.5±2.3 μmol·min$^{-1}$ was significantly lower ($p<0.0001$) than the short chain triglyceride. C4-C18:1 exhibited an initial rate of hydrolysis of 153±47 μmol·min$^{-1}$, between that of the C4 and C18:1. Overall, it is seen that all of the triglycerides are rapidly and extensively digested in the presence of porcine pancreatic lipase.

The triglycerides were next digested using the sequential SGF (RGL) SIF (PPL) model, the digestion in the SIF compartment is shown in FIG. 1*ii* A-C. No measurements were taken in the gastric compartment due to limited ionisation of the target fatty acids. Compared to when they were digested with SIF alone, the C4 and C18:1 triglycerides generally released a lower amount of titratable acid during 3 hours of digestion. The effect is largest with tributyrin, which has a significantly lower ($p<0.0001$) initial lipolysis rate 44.1±8.8 μmol·min$^{-1}$ during SGF-SIF digestion compared to SIF alone 223±59 μmol·min$^{-1}$. The total amount of acid released after SGF-SIF digestion of tributyrin 381±20 μmol, is almost ⅓ the amount released after SIF only digestion, 958±12.5 μmol. These results clearly indicate that there is considerable digestion of tributyrin within the gastric compartment of the model. When sequentially exposed to SGF and SIF, the SIF lipolysis rates of the butyrate moiety containing triglycerides C4-C18:1 is 124±20 μmol·min$^{-1}$, showing a slight but not significant decrease compared to SIF alone (124±20 μmol·min$^{-1}$). The most interesting observation is the influence of secondary fatty acid chain length on the decrease in SIF lipolysis caused by RGL pre-exposure. Originally, tributyrin exhibited a 60.2% (147±7.6 μmol) decrease in total fatty acid release during SIF lipolysis after pre-exposure to RGL in SGF. In comparison, the C4-C18:1 interesterified triglycerides exhibited a 6.1% (45±7.6 μmol) decrease.

Figure 2:
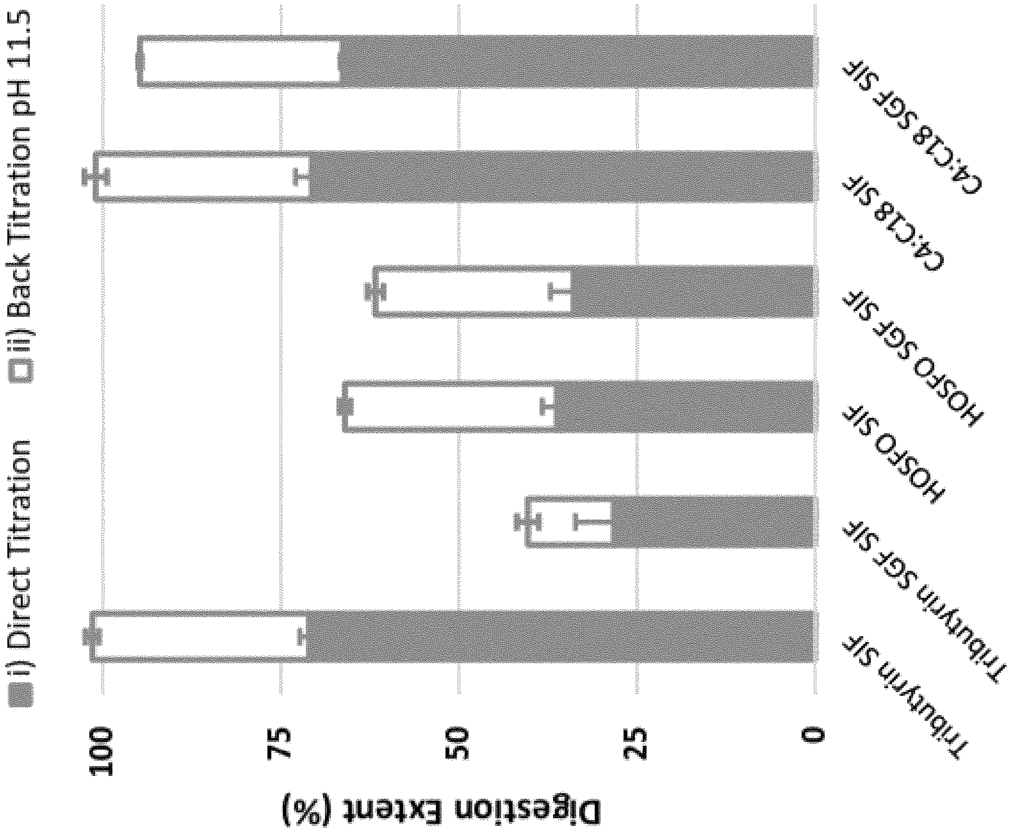
FIG. 2 shows the overall extent of lipid digestion after both SIF and SGF-SIF for tributyrin, high oleic sunflower oil and a mixture of butyrate moiety containing TAG according to the invention.

The overall extent of lipid digestion after both SIF and SGF-SIF is presented in FIG. 2 for the three triglycerides using direct and back titration. Because many fatty acids are only partially ionised at pH 6.8, direct titration gives only partial picture of the extent of lipid digestion, instead back titration to pH 11.5 or GC-FAME analysis is required to estimate the full extent of digestion. Results of the back titration for the three triglycerides show that tributyrin and the butyrate moiety containing triglycerides C4-C18:1 underwent 101.5±0.9% and 101±1.6% digestion respectively, indicating release of three fatty acids per molecule for complete digestion, whilst high oleic sunflower oil underwent 72.3±2% digestion indicating release of two fatty acids per molecule for complete digestion.

Overall, it was seen that tributyrin underwent extensive hydrolysis in the stomach, whilst high oleic sunflower oil triglyceride underwent very limited hydrolysis in the stomach. Surprisingly, it was seen that butyrate moiety containing triglycerides generated via interesterification of C4 with long chain fatty acids (C4-C18:1) decreases the extent of gastric lipolysis of C4 fatty acids. Tributyrin underwent ~60% lipolysis by gastric lipase as indicated by decreased total fatty acid release during SIF lipolysis after pre-exposure to RGL in SGF. In comparison, the C4-C18:1 butyrate moiety containing triglycerides exhibited only a 6.1% decrease in total fatty acid release in SGF-SIF. These results suggest that interesterification of C4 with long chain fatty acids (C4-C18:1) modulates the release of butyric acid within the stomach to later in the intestine following digestion, and that the design of structured lipids alter the timing (but not extent) of short chain fatty acid delivery in the gastrointestinal tract.

The invention claimed is:

1. A method for the prevention and/or treatment of non alcoholic fatty liver disease, the method comprising administering to an individual in need thereof a composition comprising compounds having the formulas (5)

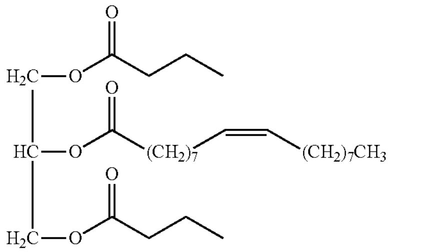

and (6)

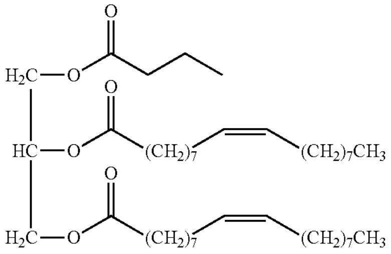

wherein the compound having formula (5) comprises at least 10% by weight of the total triglycerides in the composition, and wherein the compound having formula (6) comprises at least 10% by weight of the total triglycerides in the composition.

2. The method according to claim 1, wherein the compound having formula (5) comprises at least 15% by weight of the total triglycerides in the composition, and wherein the compound having formula (6) comprises at least 20% by weight of the total triglycerides in the composition.

3. The method according to claim 1, further comprising administering a compound having the formula (7)

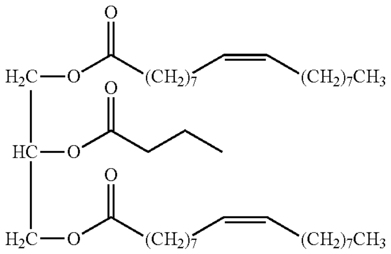

and/or a compound having the formula (8)

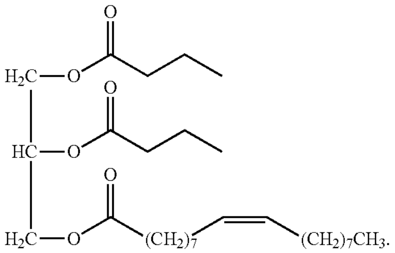

4. A method for the prevention and/or treatment of non alcoholic fatty liver disease, the method comprising administering to an individual in need thereof a composition comprising compounds having the formulas (5)

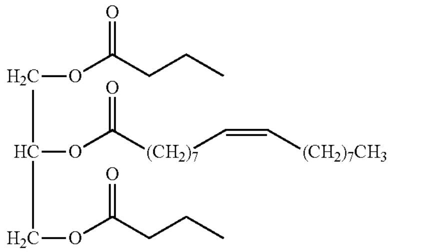

and (6)

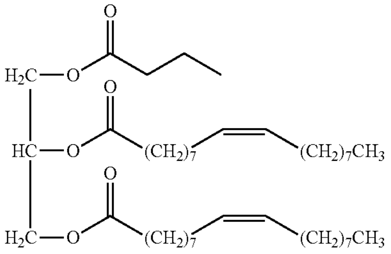

wherein the compound having formula (5) comprises at least 10% by weight of the total butyrate moiety containing triglycerides in the composition, and wherein the compound having formula (6) comprises at least 10% by weight of the total butyrate moiety containing triglycerides in the composition.

5. The method according to claim 4, wherein the compound having formula (5) comprises at least 15%, and wherein the compound having formula (6) comprises at least 20%, by weight of the total butyrate moiety containing triglycerides in the composition.

6. The method according to claim 4, wherein the composition further comprises compounds having the formulas (7)

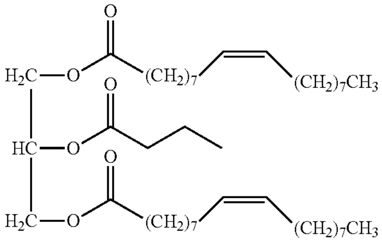

and (8)

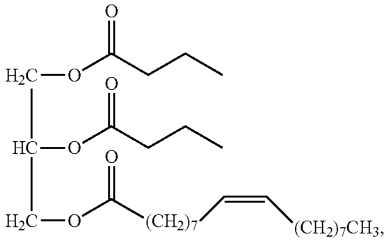

wherein the compound having formula (7) comprises at least 2% by weight of the total butyrate moiety containing triglycerides in the composition, and the compound having formula (8) comprises at least 2% by weight of the total butyrate moiety containing triglycerides in the composition.

7. The method according to claim 4, wherein the composition is a nutritional composition.

8. The method according to claim 1, wherein the composition is an infant formula, a follow-on formula or a dietary supplement.

* * * * *